United States Patent
Chen et al.

(10) Patent No.: US 10,545,099 B1
(45) Date of Patent: Jan. 28, 2020

(54) ULTRA-HIGH SENSITIVITY HYBRID INSPECTION WITH FULL WAFER COVERAGE CAPABILITY

(71) Applicant: KLA-TENCOR CORPORATION, Milpitas, CA (US)

(72) Inventors: Grace Chen, Los Gatos, CA (US); Lawrence Muray, Moraga, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 16/272,905

(22) Filed: Feb. 11, 2019

Related U.S. Application Data

(60) Provisional application No. 62/756,975, filed on Nov. 7, 2018.

(51) Int. Cl.
| | |
|---|---|
| *G01N 21/956* | (2006.01) |
| *G01N 21/95* | (2006.01) |
| *G03F 7/20* | (2006.01) |
| *H01J 37/20* | (2006.01) |
| *H01J 37/28* | (2006.01) |

(52) U.S. Cl.
CPC ....... *G01N 21/9505* (2013.01); *G03F 7/7065* (2013.01); *H01J 37/20* (2013.01); *H01J 37/28* (2013.01); *H01J 2237/2817* (2013.01)

(58) Field of Classification Search
CPC ........... G01N 21/9505; G01N 21/8806; G01N 21/9501; G01N 21/956; G01N 2021/8845; G03F 7/70633
USPC ............................................ 356/237.1–237.5
See application file for complete search history.

(56) References Cited

U.S. PATENT DOCUMENTS

| | | | |
|---|---|---|---|
| 8,204,297 B1* | 6/2012 | Xiong | G01N 21/956 356/237.4 |
| 8,455,838 B2 | 6/2013 | Shadman et al. | |
| 8,698,094 B1 | 4/2014 | Sears et al. | |
| 8,997,258 B2 | 3/2015 | Aksyuk et al. | |
| 10,026,588 B2 | 7/2018 | Werder et al. | |
| 10,126,251 B2 | 11/2018 | Lange | |
| 2006/0078191 A1* | 4/2006 | Matsumura | G01N 21/8851 382/149 |
| 2013/0088245 A1 | 4/2013 | Sezginer | |
| 2017/0177997 A1* | 6/2017 | Karlinsky | G06N 3/08 |
| 2018/0218090 A1* | 8/2018 | Liu | G06F 17/504 |
| 2018/0238816 A1* | 8/2018 | Sousa | G01N 21/95607 |
| 2019/0026879 A1* | 1/2019 | Batikoff | G06T 7/001 |
| 2019/0155164 A1* | 5/2019 | Chen | G03F 7/7065 |

* cited by examiner

*Primary Examiner* — Hoa Q Pham
(74) *Attorney, Agent, or Firm* — Kwan & Olynick LLP

(57) ABSTRACT

Disclosed are apparatus and methods for detecting defects on a semiconductor sample. An optical inspector is first used to inspect a semiconductor sample with an aggressively predefined threshold selected to detect candidate defect and nuisance sites at corresponding locations across the sample. A high-resolution distributed probe inspector includes an array of miniature probes that are moved relative to the sample to scan and obtain a high-resolution image of each site to detect and separate the candidate defect sites from the nuisance sites. A higher-resolution probe is then used to obtain a higher-resolution image of each candidate site to obtain a high-resolution image of each site to separate real defects that adversely impact operation of any devices on the sample from the candidate defects.

24 Claims, 11 Drawing Sheets

ULTRA-HIGH SENSITIVITY HYBRID INSPECTION WITH FULL WAFER COVERAGE CAPABILITY

CROSS-REFERENCE TO RELATED APPLICATIONS

This application claims the benefit of prior application U.S. Provisional Application Ser. No. 62/756,975, filed 7 Nov. 2018 by Grace Chen et al., which application is herein incorporated by reference in its entirety for all purposes.

TECHNICAL FIELD OF THE INVENTION

The invention generally relates to the field of wafer inspection systems. More particularly the present invention relates to defect detection using a ultra-high sensitivity hybrid inspection system.

BACKGROUND

Generally, the industry of semiconductor manufacturing involves highly complex techniques for fabricating integrated circuits using semiconductor materials which are layered and patterned onto a substrate, such as silicon. Due to the large scale of circuit integration and the decreasing size of semiconductor devices, the fabricated devices have become increasingly sensitive to defects. That is, defects which cause faults in the device are becoming increasingly smaller. The device needs to be generally fault free prior to shipment to the end users or customers.

Defect detection is generally implemented across a full wafer for yield management in the semiconductor manufacturing industry. Types of defects, counts of defects, and signatures found by inspection systems (or inspectors) provide valuable information for semiconductor fabrication to ensure that the manufacturing process established in the research and development phase can ramp, that the process window confirmed in the ramp phrase can be transferrable to high volume manufacturing (HVM), and that day-to-day operations in HVM are stable and under-control.

An optical inspector is currently the only viable platform in the market to deliver enough speed to economically yield full wafer inspection. Full wafer coverage with an optical inspector has been implemented for HVM due to low expected defect counts on the wafer. In a mature process, the expected defect counts are typically less than 1000. Because of these low counts, combined with the mostly random locations of the defects across a 300 mm wafer, full wafer coverage with an optical inspector has been historically used to monitor the HVM process.

As design rule shrinks, however, the sensitivity gap between what is required for defect monitoring and what can be provided by optical inspector widens. This sensitivity gap is caused by the increasing disparity between critical dimension (CD) length and optical point spread function (PSF) size. The ratio between CD and optical PSF (CD:PSF) for a current design node is less than 1:10, and the CD:PSF ratio will continue to increase for subsequent generation design nodes. Because the CD:PSF ratio today is already 1:10, a single PSF can cover several design or defect structures. As a result, one generated optical signal can come from a single source (such as DOI) inside the PSF or multiple sources (such as a combination of DOI and wafer noise artifacts or just several wafer noise artifacts) inside the PSF. This effect causes ambiguity for defect detection. For example, a similar optical signal can be generated from a bridge type defect or different types of pattern edge placement error nuisances due to a large CD:PSF ratio. This effect creates ambiguity about how the optical signal is generated. As a result, an optical inspector is not able to differentiate certain defect signals from nuisance signals, which reduces optical inspector's ability to cleanly detect DOI's. Thus, current inspection systems and methodologies have a high sensitivity defect detection performance gap.

Accordingly, there is a continued demand for improved semiconductor wafer inspector systems and techniques

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment a method of detecting defects on a semiconductor sample is disclosed. An optical inspector is used to inspect a semiconductor sample with an aggressively predefined threshold selected to detect a plurality of candidate defect and nuisance sites at a plurality of corresponding locations across the sample, and the plurality of candidate defect and nuisance sites and their locations are provided to a high-resolution distributed probe inspector. The high-resolution distributed probe inspector is used to inspect the plurality of candidate defect and nuisance sites on the sample to separate the candidate defect sites from the nuisance sites, and the high-resolution distributed probe inspector comprises an array of high-resolution probes. The high-resolution distributed probe inspector is configured to move the array of probes relative to the sample, and the array of probes are configured to scan and obtain a high-resolution image of each site to separate the candidate defect sites from the nuisance sites. A higher-resolution probe is used to obtain a higher-resolution image of each candidate site, and the higher-resolution probe has a higher resolution than a resolution of the high-resolution probes that are configured to obtain a high-resolution image of each site. Each candidate defect's higher-resolution image is reviewed to separate real defects that adversely impact operation of any devices on the sample from the candidate defects.

In a specific implementation, the high-resolution distributed probe inspector includes the higher-resolution probe. In other aspect, the optical inspector is used and configured with a resolution that is between about 300nm to 500nm, and each of the miniature high-resolution probes has a resolution that is below about 10nm. In this aspect, the array of probes can be configured to scan each site while the stage moves, and the higher resolution probe has a resolution that is about 1nm or less. In another example the sites detected by the optical inspector number in the millions and the candidate defect sites number in the thousands or less, and the high-resolution distributed probe inspector is used to inspect the plurality of candidate defect and nuisance sites on the sample to separate the candidate defect sites from the nuisance sites takes an hour or less. In another example implementation, the miniature high-resolution probes are arranged in a linear array that spans the semiconductor sample, number between 10 to 100 probes, and comprised of their own objectives and scanning electronics to scan the individual sites.

In one aspect, the high-resolution distributed probe inspector comprises a stage upon which the semiconductor sample is loaded, and the stage is configured to scan swaths of the semiconductor sample under each of the miniature high-resolution probes, which remain stationary, to provide full semiconductor sample coverage. In another aspect, the high-resolution distributed probe inspector comprises a stage upon which the semiconductor sample is loaded, and the miniature high-resolution probes are movable and configured to scan over swaths of the semiconductor sample while the stage remains fixed. In another aspect, the high-resolution distributed probe inspector comprises a stage upon which the semiconductor sample is loaded, and the stage and the miniature high-resolution probes are both movable and configured to scan swaths of the semiconductor sample under each of the miniature high-resolution probes. In a further aspect, the miniature high-resolution probes are configured to move radially while the stage is configured to rotate, and the swaths are circular. In another example, the miniature high-resolution probes are arranged in a plurality of spokes to be centered over the semiconductor sample and each spoke is configured to move radially while the stage is configured to rotate, and the swaths are circular.

In a specific embodiment, the high-resolution distributed probe inspector is a scanning electron microscope (SEM), and each probe of the miniature high-resolution probes comprises microelectromechanical system technology. In another example, the miniature high-resolution probes comprise multiple atomic force microscope (AFM) probes, multiple near-field probes, or multiple proximal optical probes.

In an alternative embodiment, the invention pertains to a hybrid inspector system for detecting defects on a semiconductor sample. This system includes an optical inspector configured to inspect a semiconductor sample with an aggressively predefined threshold selected to detect a plurality of candidate defect and nuisance sites at a plurality of corresponding locations across the sample, and the plurality of candidate defect and nuisance sites and their locations are provided to a high-resolution distributed probe inspector of the system. The high-resolution distributed probe inspector is configured to inspect the plurality of candidate defect and nuisance sites on the sample to separate the candidate defect sites from the nuisance sites, and the high-resolution distributed probe inspector comprises an array of miniature high-resolution probes. The high-resolution distributed probe inspector is configured to move the array of probes relative to the sample, and the probes are configured to scan and obtain a high-resolution image of each site to separate the candidate defect sites from the nuisance sites. The system also includes a higher-resolution probe configured to (i) obtain a higher-resolution image of each candidate site, wherein the higher-resolution probe has a higher resolution than a resolution of the high-resolution probes that are configured to obtain a high-resolution image of each site, and (ii) review each candidate defect's higher-resolution image to separate real defects that adversely impact operation of any devices on the sample from the candidate defects. The system may also be configured to perform any combination of the above-described operations.

These and other aspects of the invention are described further below with reference to the figures.

DETAILED DESCRIPTION OF EXAMPLE EMBODIMENTS

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Figure 1:
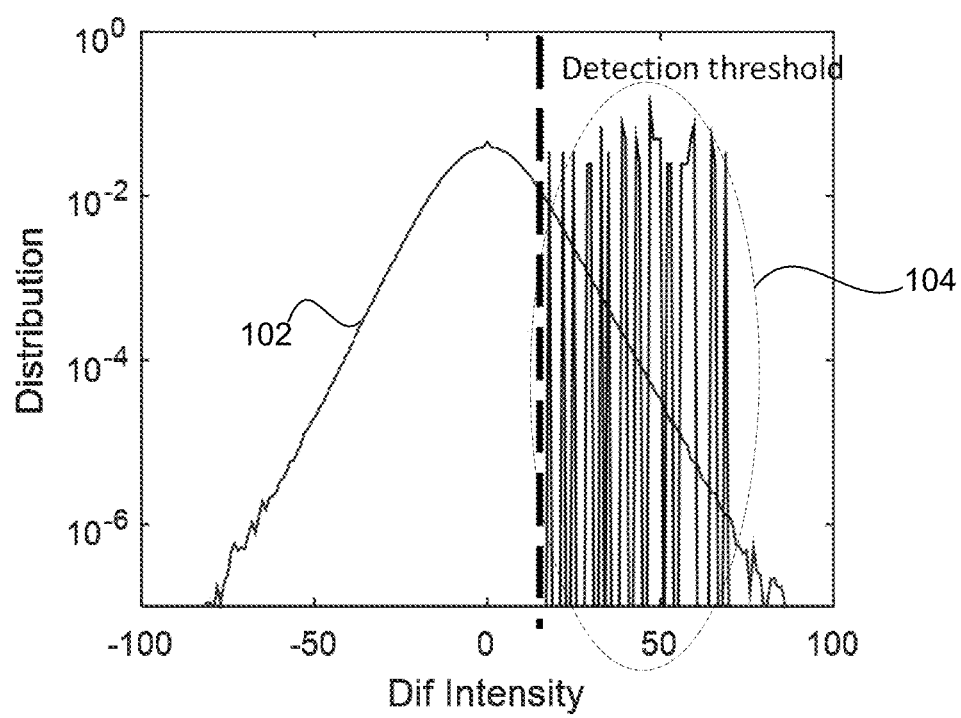
FIG. 1 is a graph of the typical background signal and typical small defect signal distribution as a function of intensity difference values.

Large CD:PSF ratios can result in signals of small defects that are always embedded in the tail end of a background distribution signal function for an optical inspector. FIG. 1 is a graph of a typical background signal distribution 102 (e.g., number of background pixels) and typical small defect signal distribution 104 (e.g., number of defect pixels) as a function of intensity difference values. As shown in this example, the small defect signals 104 can be confused with the tail end of the noise distribution 102. For example, if an optical inspection threshold is set low, a high number of nuisance signals, along with actual defect signals, are flagged as candidate defects. As semiconductor devices have increasingly reduced CD, the degree of confusion between DOI and nuisance signals becomes worse. This confusion leads to an inability for optical inspector to detect small defects with acceptable nuisance rates.

High-resolution scanning systems, such as an electron beam inspector (EBI), can be a next best solution for resolving this optical sensitivity gap. However, high-resolution scanning systems are not feasible for inspection in a high-volume manufacturing process because of inadequate wafer throughput. For example, although the resolution of EBI is high enough to resolve small semiconductor structures, EBI cannot currently deliver throughput that is acceptable for semiconductor manufacturing yield monitoring. The adoption of these high-resolution systems, such as EBI, are limited to the research and development phase due to insufficient throughput. Since high-resolution systems typically cannot provide full wafer scans, they present challenges for adoption into HVM (high volume manufacturing) inspection.

In certain embodiments of the present invention, the sensitivity defect detection performance gap is solved with a hybrid optical and a distributed high-resolution inspector system. Together the combined system changes the inspection paradigm. In general, the high-resolution system includes a fast, distributed probe architecture for quickly scanning a high number of potential defect sites. Thus, the hybrid inspector system leverages the strengths of both an optical inspector and a distributed, high-resolution system. For example, such hybrid inspector can provide detection of current design node 5 nm defects within 2 hours with full wafer coverage. Additionally, the hybrid inspector can handle a defect distribution that is random or systematic.

An aggressive threshold may be set for the optical inspector to enable at least a 5 nm defect sensitivity so that DOI's (defects of interest) can be detected in the optical scans. An aggressive threshold for the optical inspector is selected to likely result in 5-20 million candidate defect and nuisance sites from the $1^{st}$ phrase of inspection. Locations for these sites can then be sent to a high-resolution inspector for DOI/nuisance separation. To enable full wafer inspection coverage in less than 2 hours, this high-resolution inspector is operable to visit 5-20 million randomly occurring sites and perform DOI/nuisance separation in 1 hour or less. The specified site count range may vary based on the fabrication process and device design parameters. In other words, the hybrid inspection system contains (1) an optical inspector that generates enough site signals for 5nm defect detection and has the capability to scan a full wafer in less than 1 hour and (2) a high-resolution, fast inspector that has the capability to visit 5-20 million sites randomly distributed across the wafer in less than 1 hour and perform defect detection for each site visited.

Figure 2:
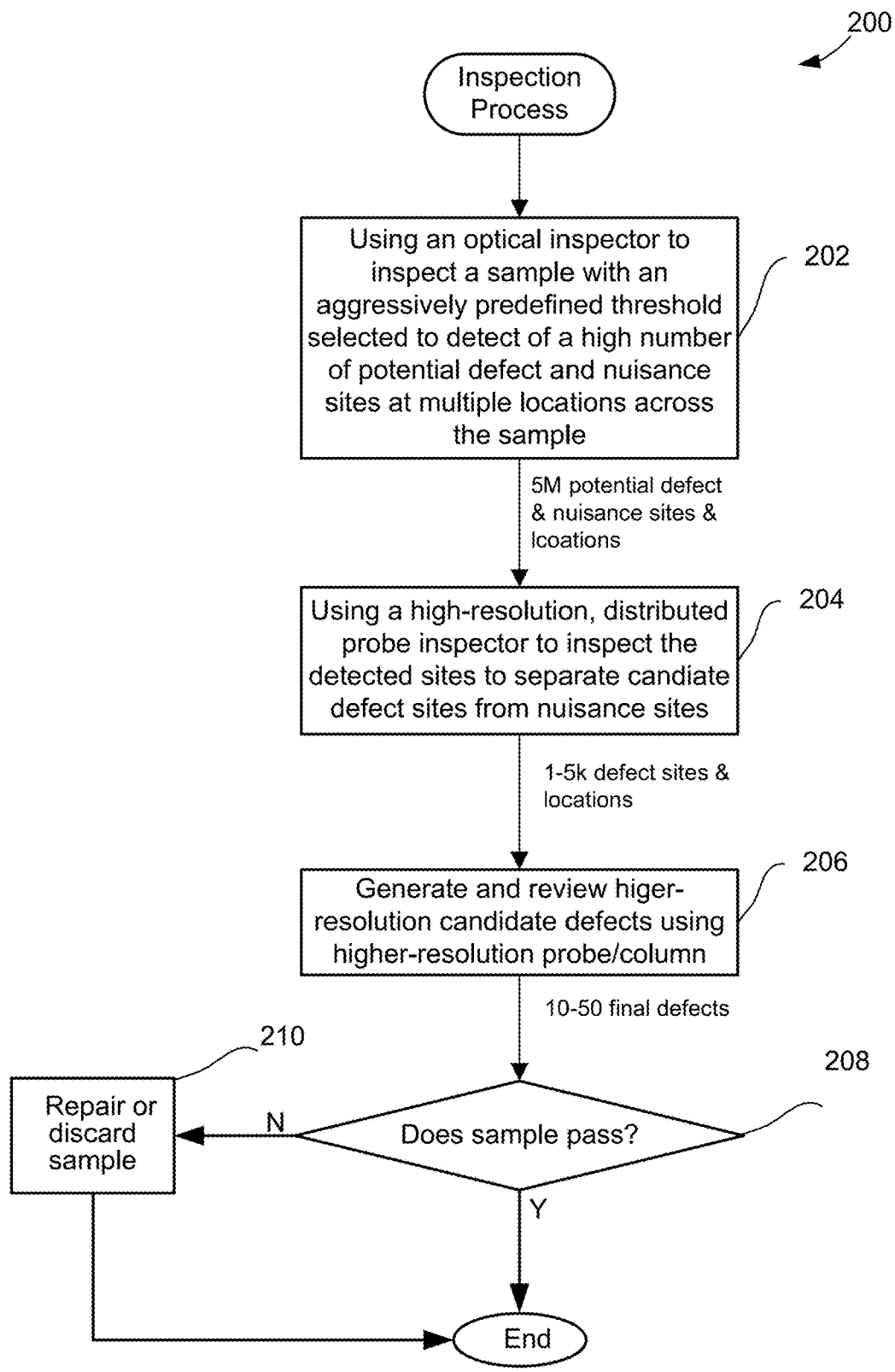
FIG. 2 is a flowchart illustrating a hybrid inspection process in accordance with one embodiment of the present invention.

FIG. 2 is a flowchart illustrating a hybrid inspection process 200 in accordance with one embodiment of the present invention. Initially, using an optical inspector to inspect a sample (e.g., semiconductor wafer) with a threshold that is selected to detect a high number of candidate defect and nuisance sites at multiple locations across the sample in operation 202. For example, the potential defect and nuisance sites number at least five million sites (number in the millions) that are typically randomly distributed across the full wafer and include more than about 1000 (e.g., typically ranging from about 1000 to 5000, or number in the thousands or less) candidate defect sites that are mixed in with the total number of detected sites.

Any suitable defect inspection technique may be utilized, such as a die-to-die, cell-to-cell, die-to-database, etc. In general, reference and test images of identically-designed wafer areas are compared, and potential defects/nuisances are flagged if the difference is greater than the aggressively predefined threshold. In general, the aggressive predefined threshold is selected to capture a defect of desired size, with the size of the desired defect depending on the design node used in the semiconductor process. For 5nm design node, the defect of interest would be around 5 nm. For more advanced design nodes, the defect of interest may be less than 5 nm.

Any suitable systems may be used to implement the $1^{st}$ phase optical tool, which can take any suitable form. For instance, the optical inspector can be operable to adjust a variety of optical parameters, such as wavelength, illumination, and polarization parameters, so that the system can generate an optimal signal for defects as small as 5nm in size different fabrication processes and structure designs. The optical inspector is also configurable to perform detection with aggressive thresholding to allow more than 200 million objects to pass through the optical stage of detection. This configuration ensures that 5 nm defects can be detected or flagged by the $1^{st}$ stage of the hybrid inspection. The optical inspector is also preferably capable of scanning a full wafer in less than 1 hour. One example tool that works well is the 2930, 2935, and 3900 inspection system available from KLA-Tencor Corp of Milpitas, Calif.

The plurality of detected candidate defect and nuisance sites and their locations are provided to a high-resolution, distributed probe inspector. The detected sites may then be inspected with the high-resolution, distributed probe inspection tool to separate candidate defects from nuisances in operation 204. For instance, 1 k to 5 k candidate defects are found and separated from the nuisance defects based on the high-resolution images provided by the distributed probe tool.

In general, the high-resolution images may be analyzed by using any suitable process to detect candidate defects, such as a die-to-die, cell-to-cell, die-to-database inspection, etc. A neural network or algorithm/model for learning defect vs. nuisance classifications and a machine learning algorithm may also or alternatively be used to differentiate defects from nuisances in this $2^{nd}$ stage. Other approaches that use complex computational methods for noise-free reference generation can also be used as the detection algorithm for the high-resolution probe system. In addition, a detection algorithm that leverages the semiconductor device design file can also be used as the detection algorithm for the high-resolution probes.

To further classify the detected DOIs into different DOI bins based on their physical morphology, a higher resolution system is used, as illustrated in 206. The positions of confirmed DOIs from operation 204 may be passed to the higher resolution probe in operation 206. The higher resolution probe has pixel resolution on the order of 1nm (or less), so that the images from the higher resolution system can be analyzed to differentiate between different types of defects, such as bridges and protrusions, for example.

In general, the review stage includes classification of defect types, including separation of "real" defects that impact yield or device function from nuisance type defect that do not impact yield or device function. Typically, 10 to 50 (or 50-100) final defects may be found in this review step. The review process may be accomplished by one or more various learning algorithms or models for classifying and separating real yield- affecting defects as real defects, including defect types (e.g., bridge, protrusion defects,), as opposed to nuisance type defects that will not impact the device function, etc.

It may then be determined if the sample passes inspection in operation 208. For example, it may be determined whether the final defects on a wafer will adversely affect the function of devices on such wafer. If the sample passes, the inspection procedure may end. For instance, the wafer sample may be further processed, diced, and packaged into packaged devices. If the sample does not pass, the sample may be repaired or discarded. For instance, certain structures may be removed or added to the wafer to eliminate effects of certain defects. Additionally, the process for fabricating a wafer may be adjusted to eliminate defects forming on subsequent wafers, for example. The procedure 200 may then end. The repaired wafer and/or subsequent wafers may be fabricated after the fabrication process adjustment.

In general, the multiple probe inspector provides high resolution in a large effective area, as opposed to high resolution in a small area as provided by a single probe system. That is, the multiple, distributed probes have multiple objectives that together provide a large effective field of view (FOV). The multiple probe inspector is configured to provide a resolution that is equal to or less than 10 nm, as compared to an optical inspector resolution that is between 200 nm to 500 nm. In a specific implementation, the multiple probe inspector provides 5-10 nm resolution for each candidate site.

Figure 3A:
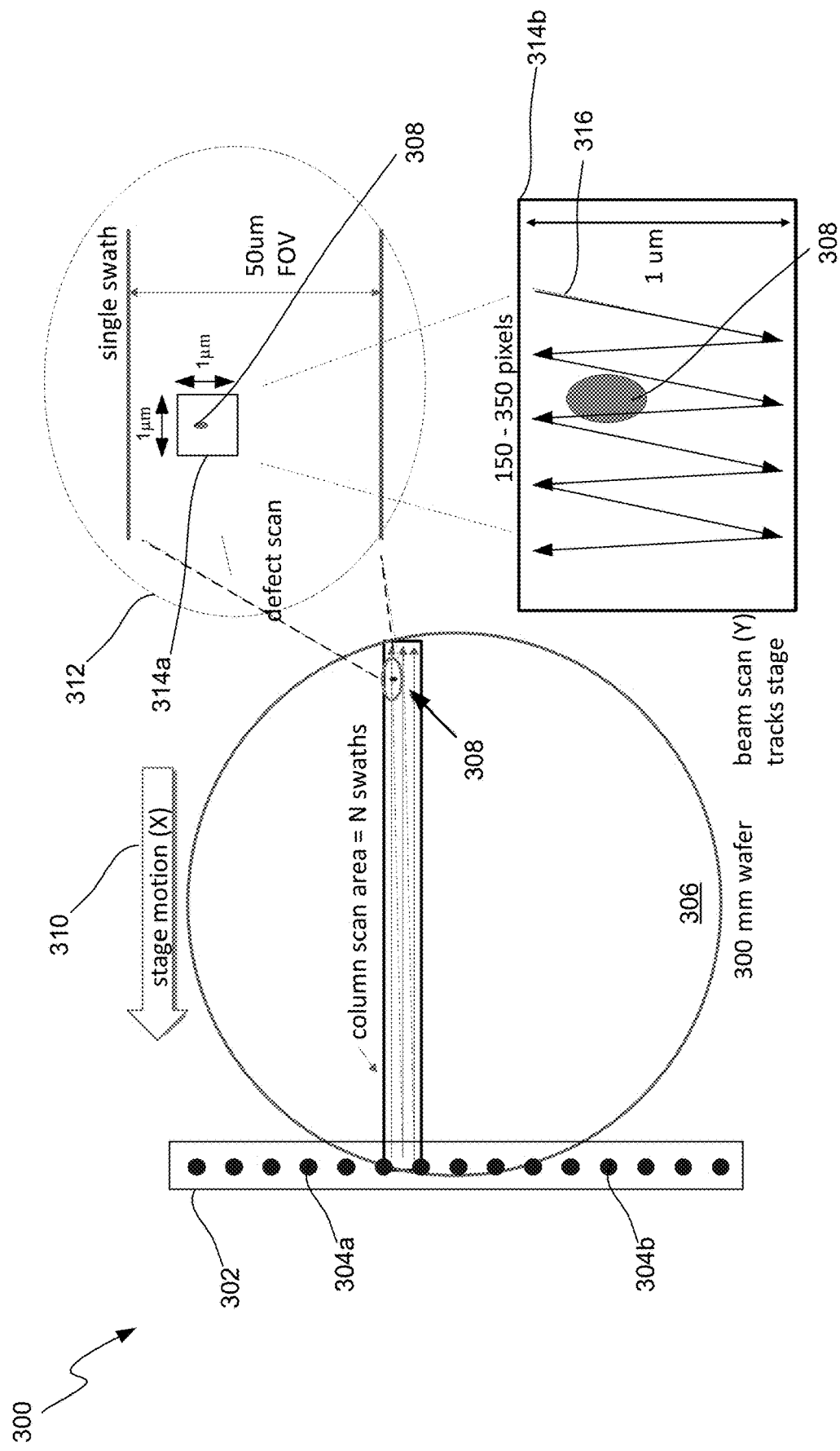
FIG. 3A illustrates a high-resolution multiple probes architecture with swathing capability and high-resolution sub-field scan in accordance with one general implementation of the presentation invention.

FIG. 3A illustrates an example of distributed probe architecture 300 that is configured with swathing and high-resolution sub-field scan capability in accordance with one general implementation of the presentation invention. The architecture 300 includes a multi-probe system 302 having a plurality of probes, such as 304a and 304b, which are arranged in a distributed manner, such as a linear array. The distributed system generally includes any suitable number of miniaturized probes with separate objectives to scan at least 5 million sites per hour. The probes also include their own scanning electronics to scan the individual sites. In the illustrated example, 30 probes are arranged so that at least 5 million sites on a wafer can be visited and inspected in less than an hour. Of course, other probe counts, such as between about 10 to 100 probes, will likely work to achieve the desired throughput as specified herein. The size of these probes is small, so the probes are most likely to be made with MEMS (microelectromechanical) techniques and components.

In one example, the wafer 306 is loaded onto a movable stage of the distributed high-resolution system 300 and the stage is configured to scan swaths of the wafer 306 under the probes, which remain stationary. For example, the stage scans a first X linear direction (e.g., 310), moves in a Y direction, and then scans another swath under the stationary probes in a second opposite X direction. The stage repeatedly scans swaths back and forth across the wafer to provide full wafer coverage. Additionally, sets of swaths from the different scans may be interleaved with each other. That is, a first set of swaths are scanned under (or by) the probe array so that the swaths have spaces in between. In other word, swath areas are skipped in the first scan. A second set of swaths are then scanned within the spaces between the first set of swaths. The swath scans are repeated to fill in the spaces between swaths until the full wafer is scanned.

In general, swaths may be skipped during each scan, and swaths may then be interleaved in separate scans. Skipping swaths may result in less damage to the wafer if the high-resolution probes is electron beam-based. Any suitable number of swaths or lines may be skipped. In general, a scan pattern that skips lines may cause less damage to certain materials such as photoresist, which tends to shrink in areas that are scanned by a charged particle beam. The number of skipped lines may be selected so that the amount of shrinkage may be comparable to line edge roughness and not significantly affect the overall line edges. Depending on the distribution of potential, skipping swath lines can be a valuable technique to both reduce detrimental effects, such as polymer shrinkage, charging, contamination, etc. and increase overall throughput.

As each swath moves under each of the probes 302, each probe is configured to scan each defect site that is present within such probes scan area. As shown, the wafer is moved through N swaths for each probe's scan area. In this example, each probe swath is about 50μm high. When a probe moves over a potential defect, such as defect 308 (also shown in expanded areas 312 and 314b), the probe may then operate to quickly scan across such defect area (defect area 314a and expanded defect area314b). As shown, an expanded view 312 is shown for the swath area that is proximate to potential defect 308. In expanded view 312, the probe's defect area 314a has a size of 1 μm by 1μm (or at most 50 μm by 1 μm) in the illustrated architecture. In the illustrated example, the probe scans in a Y direction, which is orthogonal to the wafer movement direction, which results in scan pattern 316 over a scan area resulting in 150-350 pixels being imaged for such defect 308.

The high resolution, distributed probe inspector can also take any form. For instance, each probe or column can comprise components for focus, scanning, and other suitable functions. By way of examples, the high resolution, distributed probe inspection tool is in the form of a scanning electron microscope (SEM) having multiple distributed miniature columns, multiple atomic force microscope (AFM) probes, a near-field microwave tool with multiple probes, or multiple proximal optical probes. Suitable miniaturized e-beam column technologies are further described in U.S. Pat. No. 8,698,094 B1 and U.S. Pat. No. 8,455,838 B2, which patents are incorporated herein by reference for all purposes. Viable high-resolution near-field microwave probe technology is described in U.S. patent application with Publication No. 2013/0088245, which application is incorporated herein by reference for all purposes. Example high-resolution AFM probe configurations is described further in U.S. Pat. No. 8,997,258 B2, which patent is incorporated herein by reference for all purposes.

One example high-resolution inspector for the $2^{nd}$ stage is a SEM having a column array system to achieve a throughput of 5-20 million sites in one hour or less. For instance, the SEM inspector includes a linear column array and a swathing continuously-moving precision stage. Other probe and movement arrangements are further described herein. In a specific example, each probe in the linear probe array is preferably miniaturized so the array can span the wafer. For instance, the probes can be formed from microelectromechanical system (MEMS) technology. Of course, other types of probes can be implemented as described further herein.

Each probe in a linear array (or the like) may have an imaging field of view (FOV) having a size that is roughly between 50 um ×50 um and 100 um ×100 um. Thus, a 10-probe array would have an effective FOV size of 500 um ×500 um to 1 mm ×1 mm.

During this $2^{nd}$ pass inspection, a small image patch (e.g., scan area 314 having a 1 um ×1 um in size) may be acquired when any probe crosses a location marked as a potential defect site by the $1^{st}$ stage optical inspector. Within its FOV, each probe can be configured with independent two-dimensional positioning steering that allows maximization of the number of sites visited as the stage moves with a constant velocity. Each probe is also preferably operable to independently track stage motion, resulting in high quality defect images.

In one implementation the array or probe can be a miniature electron beam column. Under this implementation, with the stage moving at constant stage speed of 50 mm/s and targeted electrons per pixel (e/p) being greater than 1500 with a 5 mn pixel size, a distributed miniature electron beam column with 10 columns can cover at least 5 million sites per hour, for example on a 300 mm wafer in less than 1 hour. In general, the $2^{nd}$ stage inspector can cover 5-20 million (or more) randomly distributed sites and generate high resolution images of such sites so that DOI and nuisance sites can be differentiated. The throughput capability can be met with various spot sizes, such as 4 nm, 7 nm, 10 nm, and15 nm spot diameters. In certain MEMS-based column array inspector embodiments, the spot diameter of each MEMS-based column is designed to be in the range of 4-15 nm. Table 1 below shows the throughput calculation of 5 million randomly distributed sites being achieved for 10 MEMS-based columns, each with independent beam steering capability. With the addition of more MEMS-based columns, an even higher number of sites can be covered although not required.

TABLE 1

| N Sites Across Wafer | N MEMS-based columns |
|---|---|
| 5,000,000 | 10 |
| 10,000,000 | 20 |
| 50,000,000 | 100 |

Figure 3B:
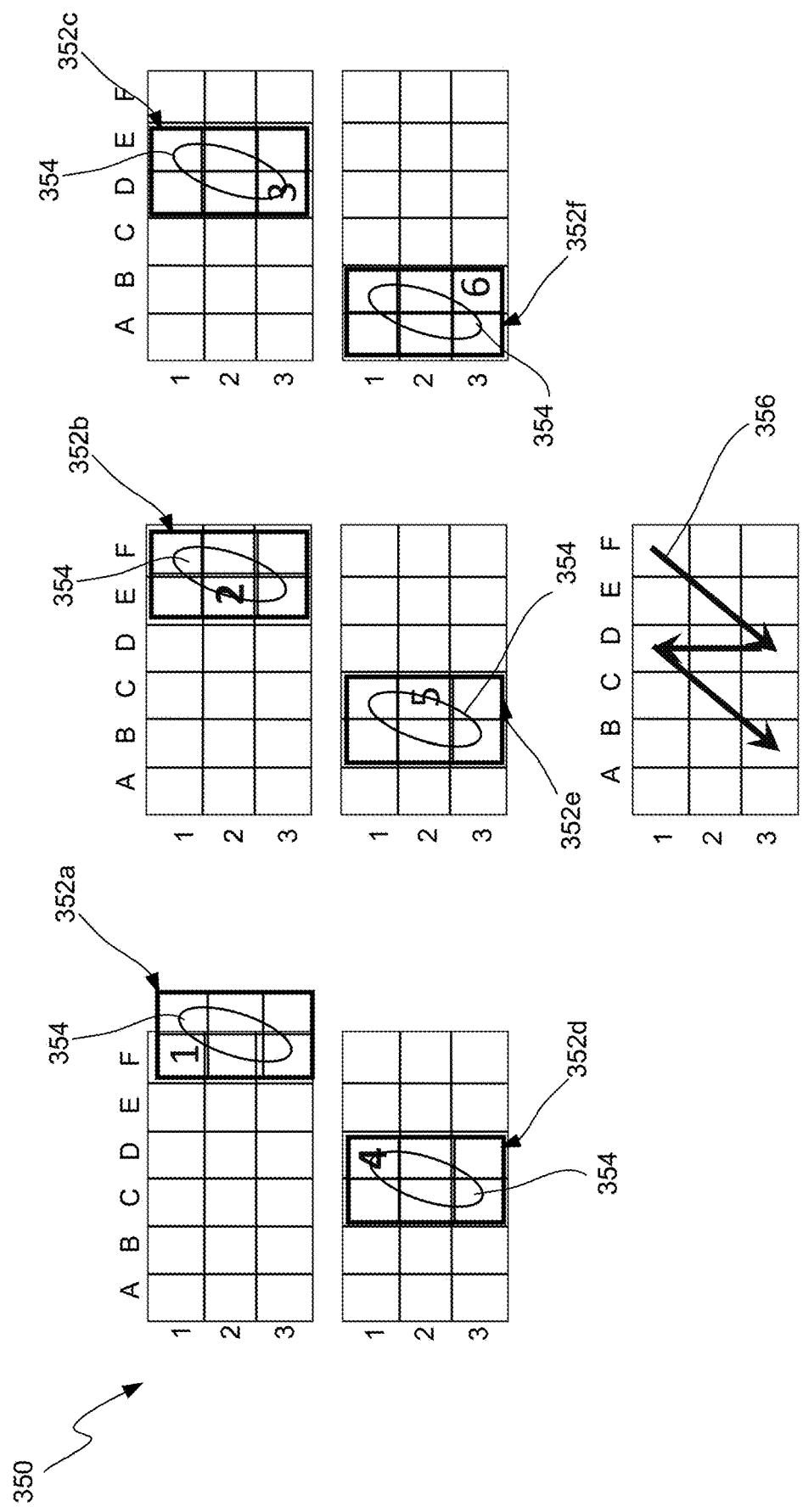
FIG. 3B illustrates a simplified track mode technique for scanning a defect with an electron beam while the stage moves underneath in accordance with one embodiment of the present invention.

FIG. 3B illustrates a simplified track mode technique 350 for scanning a defect with an electron beam while the stage moves underneath in accordance with one embodiment of the present invention. In track mode for an electron beam column implementation, the beam moves as the wafer moves (for high throughput). In this example, the beam is emitted from a probe (or column) of an array that is in a fixed position. The column scan field is represented by a grid having columns A-F and rows 1-3. Each grid position can correspond to a pixel. The defect 354 is contained in a defect area having a size that is 2 columns×3 rows (or 2 by 3 pixels).

Initially, the stage moves the defect to position 352a with respect to the column scan field so that the defect area is aligned to the right edge of the column scan field and data is acquired for scan field position Flat time step 1. Next, the stage moves the defect area one pixel to the left to position 352b, and the beam moves one pixel down and one pixel to the left to acquire data for scan field position E2 at time step 2. Again, the stage moves the defect area one pixel to the left to position 352c, and the beam moves one pixel down and to the left (the "tracking") to acquire data for scan field position D3 at time step 3. Next, the beam moves back to the top (retrace), and the stage moves the defect area one pixel to the left to position 352d and data is acquired scan field position D1 at time step 4. This process continues for defect area being positioned at 352e and 352f for which the beam moves to acquire data at scan field position C2 at time 5 and position B3 at time 6, respectively. After the 6 time steps, the defect is completely scanned by beam movement 356.

Figure 3C:
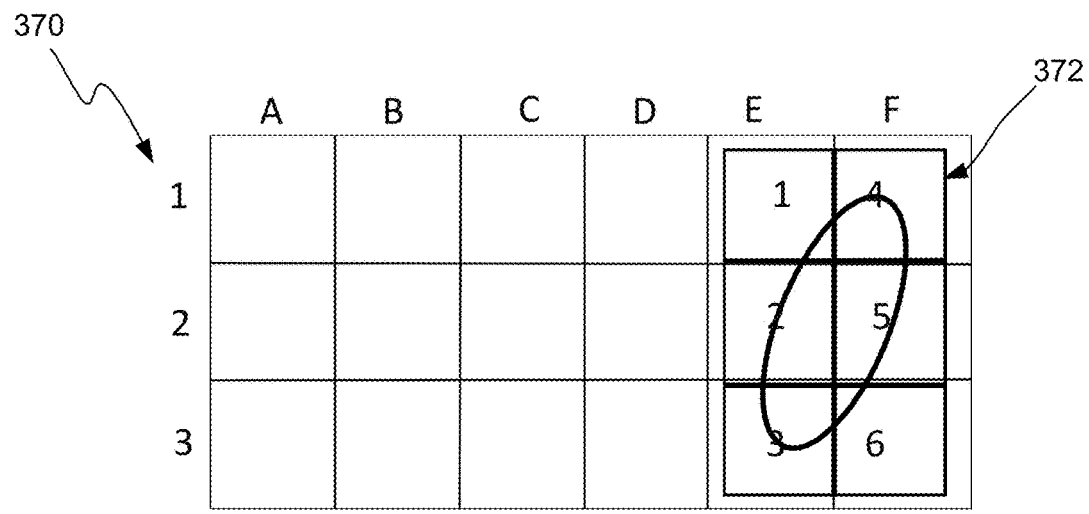
FIG. 3C illustrates a simplified frame mode technique.
Figure 3C:
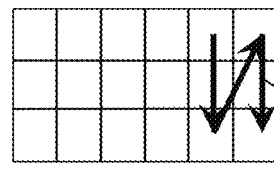

The above-described track mode technique represents an improvement (e.g., significantly increased throughput) over the frame mode and swath mode technique. FIG. 3C illustrates a simplified frame mode technique 370. In frame mode, the defect area is parked underneath the column scan field, and the beam moves in pattern 376. The defect is scanned by the beam, which moves to each pixel of the defect area in a time sequence 1-6 so that data is acquired at times 1-6.

Figure 3D:
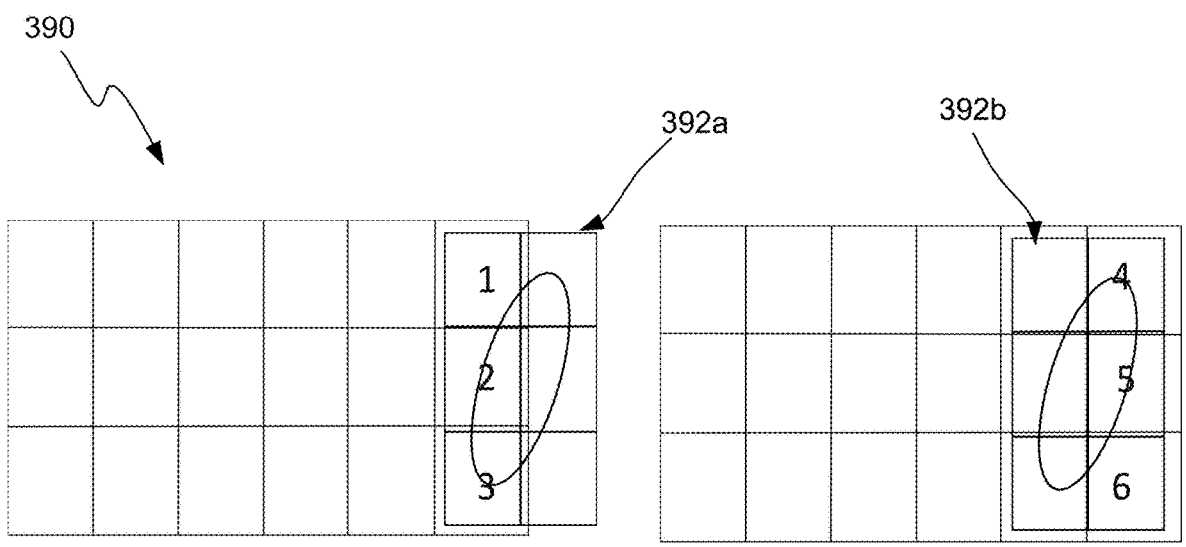
FIG. 3D illustrates a simplified swath mode technique.
Figure 3D:
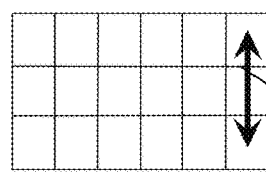

FIG. 3D illustrates a simplified swath mode technique 390. In swath mode, the wafer defect area is aligned to the right edge of the column scan field and stopped at position 392a. The column scans from top to bottom (pattern 396) at time steps 1-3; records the information; and then moves back to the top. At the same time the wafer advances one pixel to the left to position 396b and aligns with the second row of wafer pixels to the left edge of the column scan. The column then scans down again (pattern 396) in time steps 4-6 to capture the last 3 wafer pixels.

In certain embodiments, the time for scanning all defects cannot exceed the time spent to swath the wafer, and the effective scan length of the stage movement cannot exceed the FOV size of the columns. The column minimum footprint can be limited by crosstalk, which can also put a limit on the maximum number of columns and greatest throughput that is achievable.

Figure 4A:
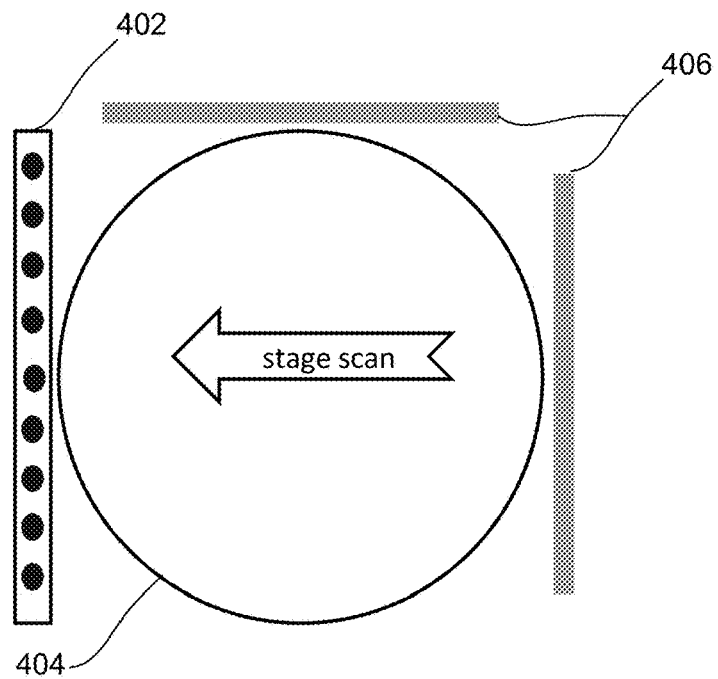
FIG. 4A illustrates an array of high-resolution probes having a fixed position and a wafer that is moved under such high-resolution probe in accordance with one embodiment of the present invention.
Figure 4B:
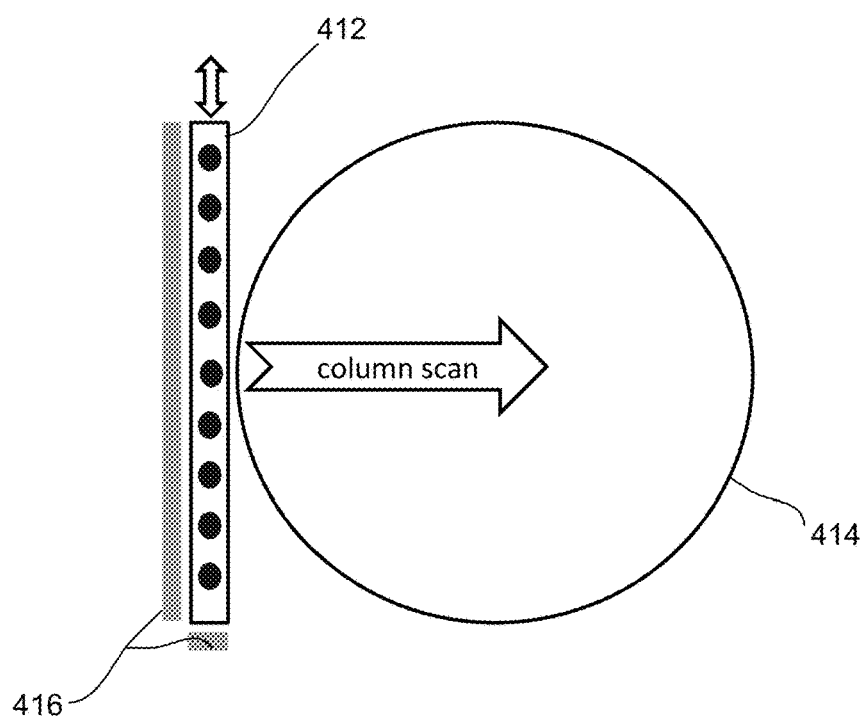
FIG. 4B shows a schematic of an array of high-resolution probes system that is operable to move relative to a fixed wafer in accordance with an alternative embodiment of the present invention.
Figure 4C:
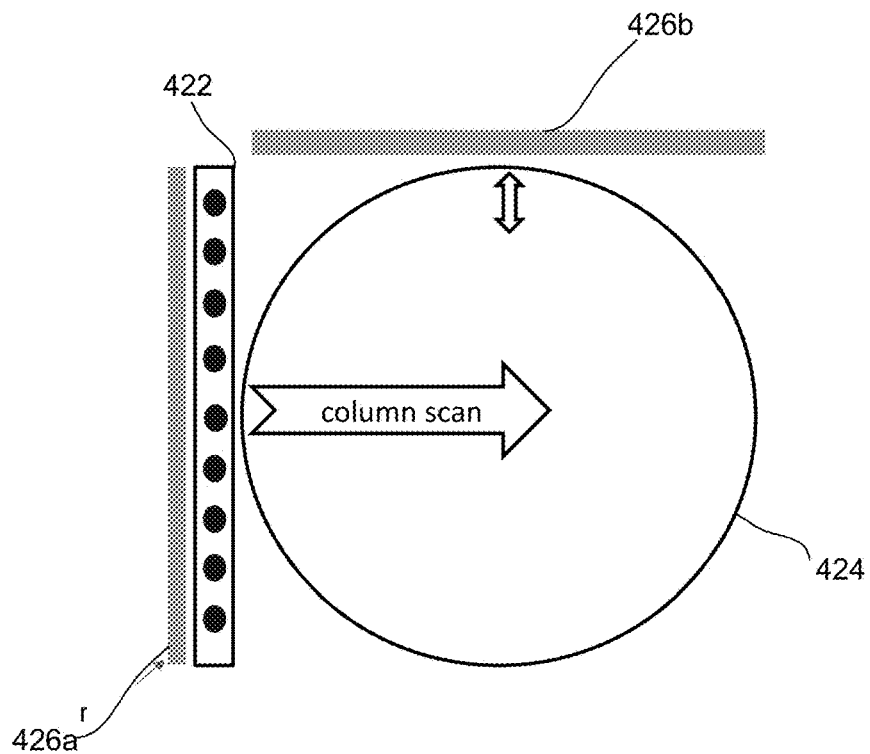
FIG. 4C shows an array of high-resolution probes that is operable to move relative to the wafer, which is moved in a direction orthogonal to the probe movement direction, in accordance with another alternative embodiment of the present invention.
Figure 4D:
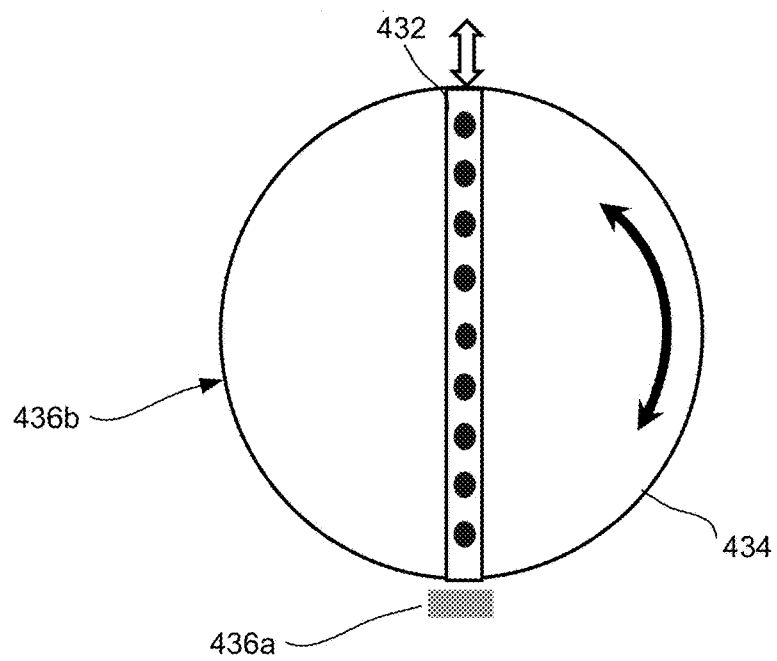
FIG. 4D illustrates an array of high-resolution probes that moves along a single axis, while the stage and wafer rotate, in accordance with yet another embodiment of the present invention.
Figure 4E:
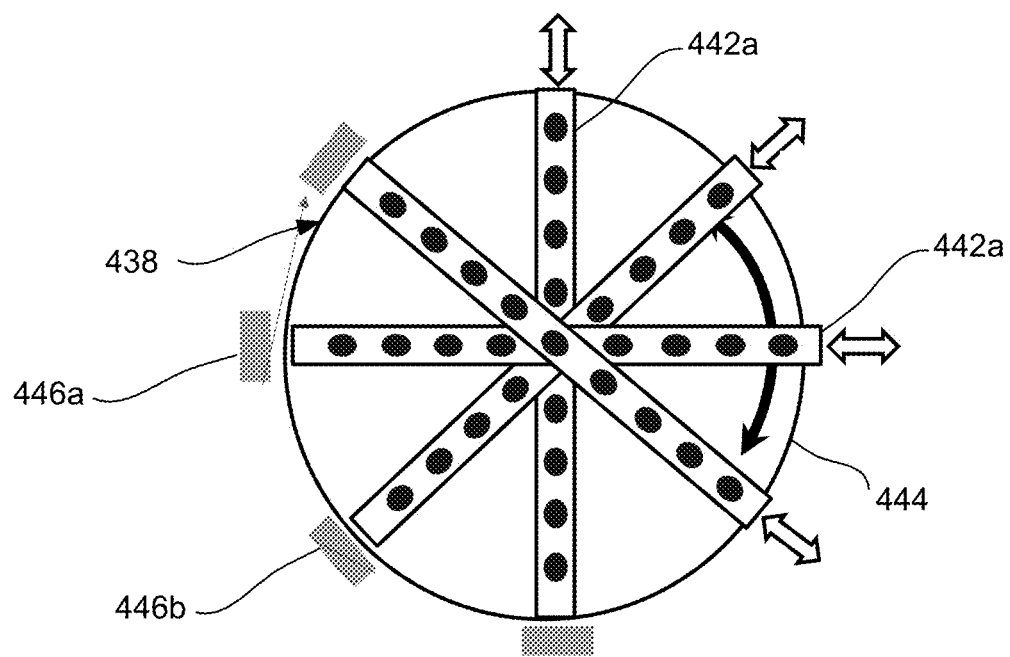
FIG. 4E illustrates a spoke arrangement of sets of linear arranged high-resolution probes with radial movement and a wafer with rotational movement in accordance with another embodiment of the present invention.

The $2^{nd}$ stage inspector can be configured to scan the candidate sites in any suitable manner. FIG. 4A-4E illustrate various $2^{nd}$ stage inspector configurations and scanning techniques. In all cases, the $1^{st}$ stage inspector provides location coordinates for each potential defect/nuisance site, and the inspector operates to precisely move to each potential site on the sample by various location determination mechanisms. This can be achieved by moving the stage as shown in FIG. 4A, moving the array of probe as shown in FIG. 4B, moving both the stage and the array of probe as shown in FIG. 4C, or rotating the stage as shown in FIG. 4D and 4E. To precisely trace the probe position steering the motion of either the stage or the rail of the array, a laser interferometer feedback mechanism can be used for fine tuning of probe positioning. The laser interferometer can be mounted on either the stage or on the array of the probes. Each probe's fine position tuning is operated independently to achieve the highest position accuracy for each probe. In all of these examples, each probe is configured to scan each candidate site in its respective swaths.

FIG. 4A illustrates a linear array of probes 402 having a fixed position and stage 404 with a wafer thereon that moves under the fixed probes 402 in accordance with one embodiment of the present invention. In this embodiment, the inspector may also include a pair of interferometers 406 for accurately determining the wafer position with respect to each probe. More laser interferometers may be used as needed. The interferometers are positioned along both the X and Y axis of the stage to track both directions. Additional laser interferometers may be used to track the location of the probes. This could be a minimum of two (X&Y) up to a maximum of one per probe. Z-height mapping may also be implemented using a static height map or dynamically with a sensor positioned at each probe. For example, the z-height sensor may be optical in order enable height mapping of any surface. The depth of focus of a single probe alone may not be sufficient to compensate for the variations in the sample height.

This embodiment also includes a relatively large chamber to accommodate the stage movement for moving the wafer back and forth under the probes. Additionally, the stage scans back and forth across the wafer so that this arrangement is associated with a turnaround time and vibrations caused by de-accelerations and accelerations.

FIG. 4B shows a distributed probe system that is operable to move relative to a fixed wafer stage in accordance with an alternative embodiment of the present invention. As shown, the linear probe array 412 moves and scans in a probe scan direction as indicated in FIG. 4B, while the stage and wafer 414 remain in a fixed position. Additionally, the inspector may include N-axis interferometers (e.g., 416) for determining locations along N number of axis. In this embodiment, the chamber can be relatively small since the stage is stationary while the probes merely scan over such stage. However, the probes may use moving bellows to achieve 2D movement. This embodiment also has associated turnaround time and vibration effects.

FIG. 4C shows a linear array of probe system 422 that is operable to move relative to the wafer stage 424, which moves orthogonal to the probe movement direction, in accordance with another alternative embodiment of the present invention. In this example, a first interferometer mirror 426a is mounted with the probes to track movement and position in one direction, while a second mirror 426b is mounted with the stage 424 to track movement and position in another, orthogonal direction. Of course, the inspector may include additional interferometers for tracking other movement directions, such as Z, tilt, or rotation. This implementation is associated with a small chamber, low mass, and low Abbe errors, as well as a slow stage scan. However, the probes may use bellows to achieve 1D movement. This embodiment also has associated turnaround time and vibration effects.

FIG. 4D illustrates a probe array 432 that moves along a single axis, while the stage and wafer 434 rotate, in accordance with yet another embodiment of the present invention. This system includes at least one radial interferometer mirror 436a for tracking the probe movement and position, as well as a high-precision rotary encoder 436b for tracking the stage's movement and position. Of course, the inspector may include additional interferometers for tracking other movement directions. This embodiment also does not have any associated turnaround time or vibration effect since the beams scan back and forth, while the wafer simply spins without accelerating or deaccelerating during inspection.

FIG. 4E illustrates a spoke arrangement of linear probe arrays and rotating stage in accordance with another embodiment of the present invention. As shown, the probe arrays (e.g., 442a and 442b) are each arranged at a fixed spoke position around the wafer stage 444, and each array is movable along a radial direction. The stage and wafer 444 are configured to rotate underneath the probe spokes, which move radially while the wafer rotates. The inspector may also include radial mirrors (e.g., 446a and 446b) for tracking the probe movement and a high-precision rotary encoder 448 for tracking the stage's movement and position. This embodiment may be associated with a small chamber, low mass, low Abbe errors, and moving bellows for 2D movement. This embodiment also does not have any associated turnaround time or vibration effects since the beams scan back and forth, while the simply wafer spins.

The dual stage system embodiments described herein may be implemented in any suitable manner. FIGS. 5A-5D show variations of a hybrid inspection system (500, 520, 530, 540), in accordance with several embodiments of the present invention. In all the figures, the combined inspector includes a robotic wafer handling system 502, an optical inspector 504, a high-resolution, distributed inspector 506, a wafer load position 508, and a wafer load position 510, respectively. The robotic wafer handling system 502 is configured to transfer wafers to and from the optical inspector 504 and high-resolution, distributed inspector 506 as well as to and from the wafer load positions 508 and 510. The optical inspector 504 is configured to detect potential defects sites, which includes nuisance sites, as described above. The high-resolution, distributed inspector 506 is configured to quickly scan the sites to distinguish the potential defects from the nuisance sites. The wafer load position 508 and wafer load position 510 are configured to hold one or more wafers. In most cases, they hold a plurality of wafers. The wafers may be from the same lot or from a different lot.

Figure 5A:
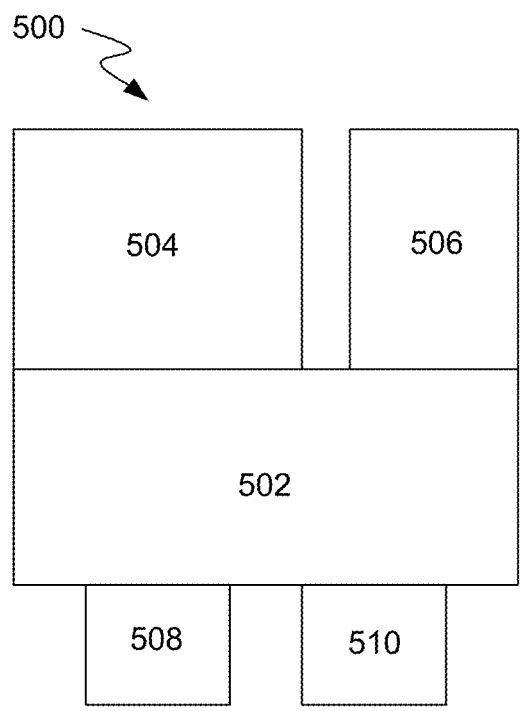
FIGS. 5A-5D show variations of a hybrid inspection system, in accordance with several embodiments of the present invention.
Figure 5B:
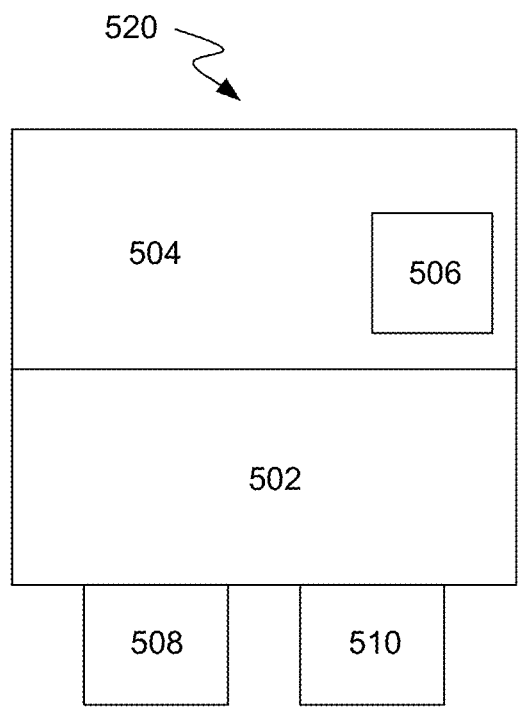
Figure 5C:
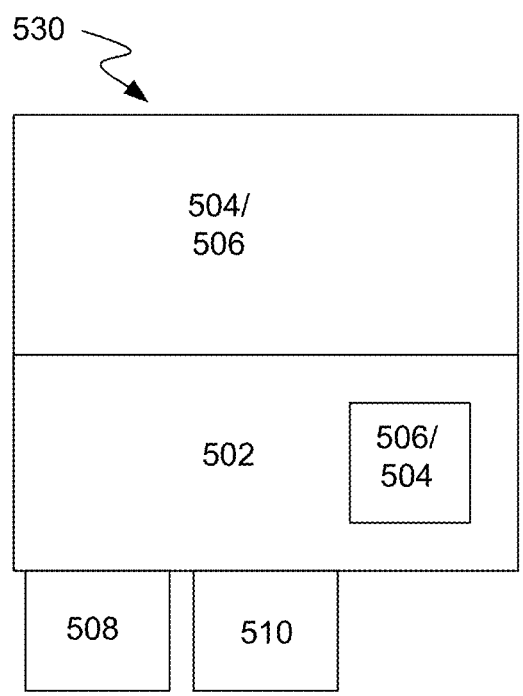
Figure 5D:
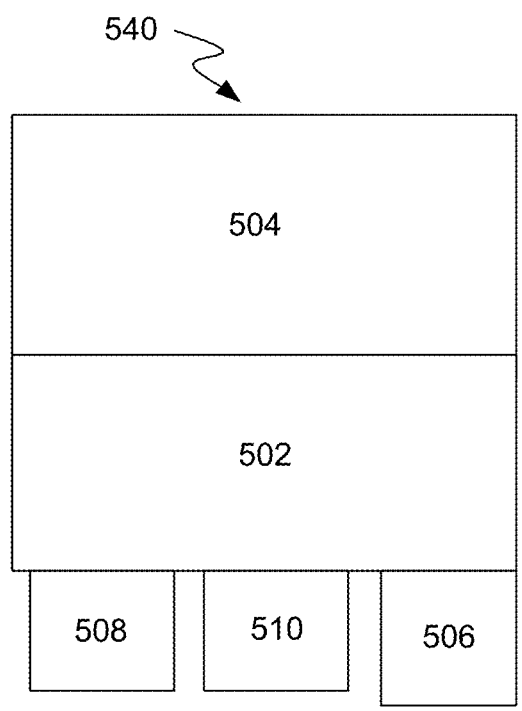

In FIGS. 5A and 5D, the optical inspector 504 and the high-resolution, distributed inspector 506 are separate systems that are integrated via the robotic wafer handling system 502. In FIG. 5B, the high-resolution, distributed inspector 506 is integrated into the optical inspector 504 or vice versa. In FIG. 5C, the high-resolution, distributed inspector 506 or optical inspector 504 is integrated into the robotic wafer handling system 502 with the other inspector 504/506 being separate from the wafer handling system 502.

In one operation, some of the wafers from wafer load position 508 and/or 510 have potential defect and nuisance sites detected at the optical inspector 506 and, thereafter, have high-resolution images of the sites generated at the high-resolution, distributed inspector 506 for separating potential defects from nuisance sites. The wafer can be inspected by both inspectors without being removed from the system, e.g., the wafer handling as well as the throughput issues associated therewith are reduced.

If the optical inspector is integrated with a distributed, high-resolution system in the form of an SEM system, both inspectors may share a same vacuum chamber. However, only a single smaller vacuum chamber is needed for a standalone SEM inspector.

Certain embodiments of such a combined system allows 5 nm full wafer inspection sensitivity in less than 2 hours. The hybrid inspector system leverages the strengths of an optical inspector and high-resolution system. Together, the inspectors of this hybrid system provide a solution that neither optical inspector nor high-resolution inspector can achieve alone, which will solve the industry performance gap. In sum, a high sensitivity, high throughput hybrid inspector, enabling 5 nm defect sensitivity across 300 mm wafer in less than 2 hours, is provided in certain implementations. The $1^{st}$ stage optical inspector can make use of an aggressive threshold inspection to allow DOIs to be detected by the optical inspector stage, and the $2^{nd}$ stage inspector then uses high resolution for DOI and nuisance differentiation of the sites detected in the $1^{st}$ stage.

Any suitable optical inspection tool may be implemented for detecting a high number of potential defect and nuisance sites in a $1^{st}$ stage as described herein. Certain inspector tool embodiments provide flexible wavelength selection in order to cover a vast range of wafer material properties and structures. Additionally, the inspection tool may be operable to provide shorter wavelengths and may include flexible polarization selection in order to obtain the best signal. The inspection system may also be operable to collect more information in one scan to improve the inspection throughput, defect classification, nuisance suppression.

In general, applicable optical inspection tools for implementation of techniques of the present invention may include at least one light source for generating an incident light beam at selected wavelengths to detect defects in different material types and structure types. Such an inspection may also include illumination optics for directing the incident beam to the area-of-interest, collection optics for directing an output beam that is emitted from the area-of-interest in response to the incident beam, a sensor for detecting an output beam and generating an image or signal from the detected output beam, and a controller for controlling the components of the inspection tool and facilitating defect detection.

In one embodiment, an inspection tool includes illumination and collection modules for generating and collecting light at a wide range of wavelengths (above 190 nm -950 nm). The inspector tool may also provide polarization options for parallel and perpendicular e-field and a set of sub-band wavelength filters for applying across the wavelength range for each of the long and short wavelength paths.

Figure 6:
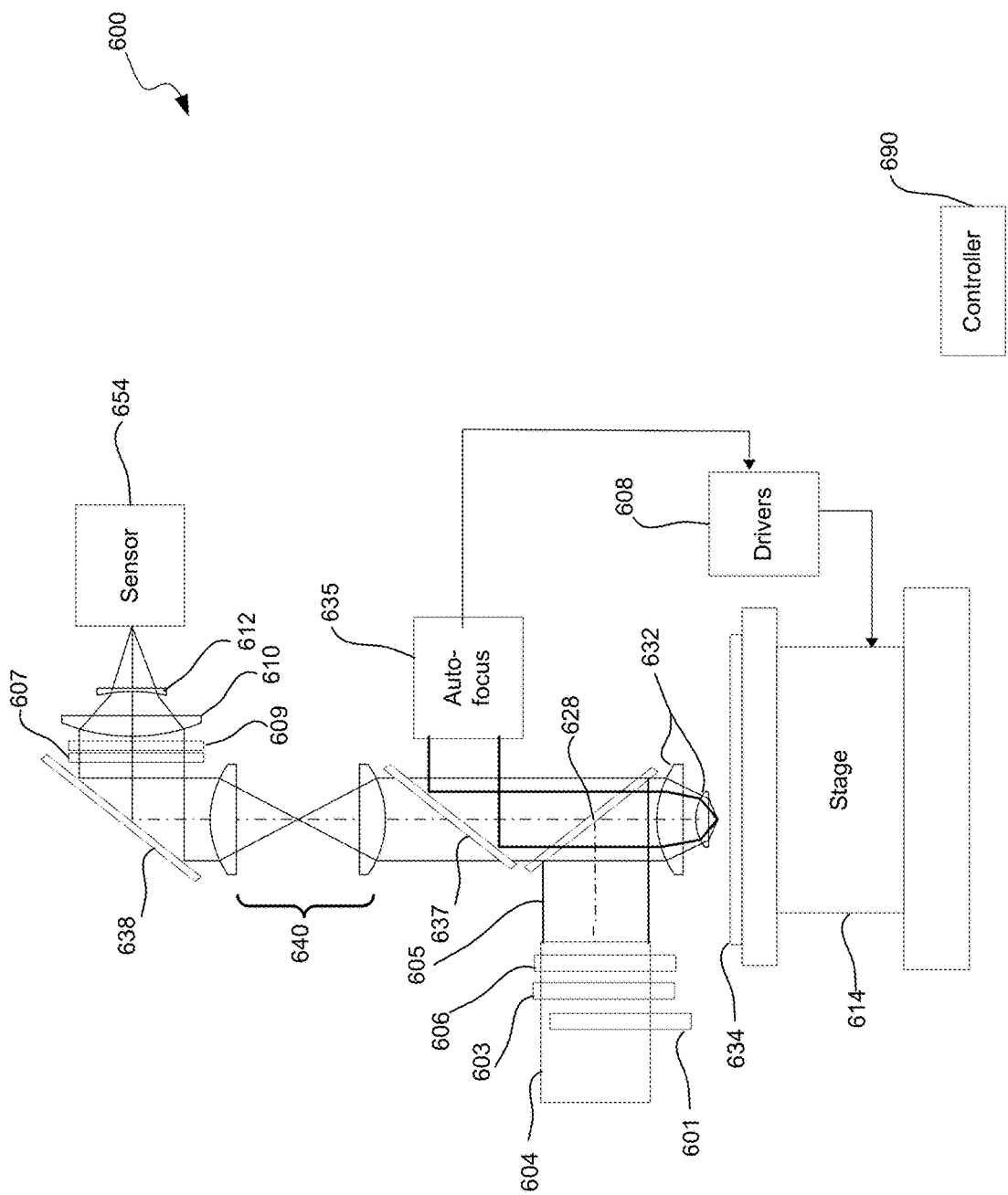
FIG. 6 is a diagrammatic representation of an optical inspection system in accordance with a specific implementation of the present invention

FIG. 6 is a diagrammatic representation of an optical inspection system 600 in accordance with a specific implementation of the present invention. As shown, the system 600 includes a broadband light source (e.g., illuminator 604) which generates illumination light 605. Examples of light sources include a laser-driven light source, a high-power plasma light source, a transillumination light source (e.g., halogen or Xe lamp), a filtered lamp, LED light sources, etc. The inspection system may include any suitable number and type of additional light sources, besides broadband light sources.

The incident beam from the light source may generally pass through any number and type of lenses which serve to relay (e.g., shape, focus or adjust focus offset, filter/select wavelengths, filter/select polarization states, resize, magnify, reduce distortion, etc.) the beam towards a sample on stage 614 coupled with drivers 608.

The illuminator 604 may include any suitable optical elements for generating an incident beam having selected wavelength ranges. For example, the illuminator 604 may include a filter wheel 601 with selectable bandpass filters that are individually inserted (or rotated) into the illumination path to change the wavelength of the illumination beam. Generally, each inspection wavelength range may be selected based on optimization of its illumination and collection pupil aperture shapes, polarization of the incident and collection path, magnification, pixel size, or any combination thereof.

The illuminator may also include one or more additional spectral filters (e.g., 603) that may be used to further define the spectrum of the incident beam. For example, each spectral filter can further be used to optimize the sensitivity for the defects that are intended to be captured. A separate polarizing filter 606 can also be selectively positioned in the incident beam path to further optimize the inspection sensitivity for different wavelength ranges.

A pupil relay (not shown) may also be used to reimage the incident light and focus the pupil onto the system pupil at the objective lens 632. A 50-50 beam splitter 628 may be used to send the light to the objective lens 632. The 50-50 beam splitter 628 may also be arranged to send light reflected or scattered from the sample toward collection optics. A pupil that is conjugate to the system pupil (located at the objective lens) may be used in the incident beam path. Each pupil or aperture can have a specific shape to obscure parts of the light path to maximize the signal for the selected wavelength range.

The objective lens 632 is preferably optimized for all selectable wavelengths that are used for defect detection. For instance, the objective 632 has a composition, including lens coatings, and arrangement for correction of color aberration.

In an alternative embodiment, the objective lens 632 may be an all reflective objective or refractive or a combination (catadioptric) configuration.

The resulting output beam reflected or scattered from the sample may then be received by another dichroic beam splitter 637, which may be arranged to insert an autofocus into the objective lens 632 via auto-focus system 635. The autofocus beam may have a wavelength that is separated from the different inspection bands. The wavelength for the autofocus can be varied as long as it is not in the inspection wavebands for any of the selected inspection wavelength ranges. Cost and availability of components can affect where the auto-focus insertion is located. The autofocus wavelength band may be 40 nm or less to minimize focus plane change due to wafer material response. For instance, the auto-focus system 635 may use an LED light source. The dichroic beam splitter 637 may be arranged to reflect the autofocus waveband and transmit all light above and below that region. The 50-50 beam splitter 628 can also be configured to pass the autofocus light with high efficiency (e.g., by use of a coating). This element may improve the light efficiency of the auto-focus by nearly 4×.

If the autofocus wavelength is much higher than the selectable inspection wavelength ranges, the autofocus beam will be affected by different thermally induced focus change than the inspection imaging system. The system may include mechanisms to provide feedback on the focus change due to environment (temperature, pressure), lens heating, etc. By way of examples, they auto-focus system 635 may include feedback mechanisms in the form of temperature and pressure sensors and a calibration wafer installed on the side of the wafer chuck for evaluating the focal plane change. Based on feedback, the auto-focus system 635 may adjust one or more of the lens elements (such as by moving lenses to form an adjustable air gap) to introduce focus correction. The frequency of the correction can also be determined based on such feedback.

The output beam may be directed and shaped by any suitable number and type of collection optics, such as pupil relay (lens group 640) and, mirror 638, a polarizer 607, aperture 609, and optics elements 610 and 612 for zooming and focusing the output beam onto sensor 654. By way of example, the sensor 654 may be in the form of a CCD (charge coupled device) or TDI (time delay integration) detector, photomultiplier tube (PMT), or other sensor.

The pupil relay 640 may be designed to form an image of the system pupil (at the objective lens 632) for the purpose of inserting specific apertures (609) in the collection path to optimize the inspection sensitivity for each wavelength range. Different aperture settings may be selected to achieve different angles of incidence on the sample. A polarizing filter (605 or 607) may be positioned in the illumination or collection path for the purpose of also optimizing the inspection sensitivity.

The system may also include a controller or computer system (e.g., 690). For instance, the signals captured by each detector can be processed by controller 690, which may include a signal processing device having an analog-to-digital converter configured to convert analog signals from each sensor into digital signals for processing. The controller may be configured to analyze intensity, images, phase, and/or other characteristics of the sensed light beam. The controller may be configured (e.g., with programming instructions) to provide a user interface (e.g., on a computer screen) for displaying resultant test images and other inspection characteristics as described further herein. The controller may also include one or more input devices (e.g., a keyboard, mouse, joystick) for providing user input, such as changing wavelength, polarization, or aperture configuration, viewing detection results data or images, setting up an inspection tool recipe.

Techniques of the present invention may be implemented in any suitable combination of hardware and/or software. The controller typically has one or more processors coupled to input/output ports, and one or more memories via appropriate buses or other communication mechanisms.

The controller may be any suitable combination of software and hardware and is generally configured to control various components of the inspection system. For instance, the controller may control selective activation of the illumination source, the illumination or output aperture settings, wavelength band, focus offset setting, polarization settings, etc. The controller may also be configured to receive the image or signal generated by each detector and analyze the resulting image or signal to determine whether candidate defects/nuisances are present on the sample, characterize defects present on the sample, or otherwise characterize the sample. For example, the controller may include a processor, memory, and other computer peripherals that are programmed to implement instructions of the method embodiments of the present invention.

Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

Figure 7:
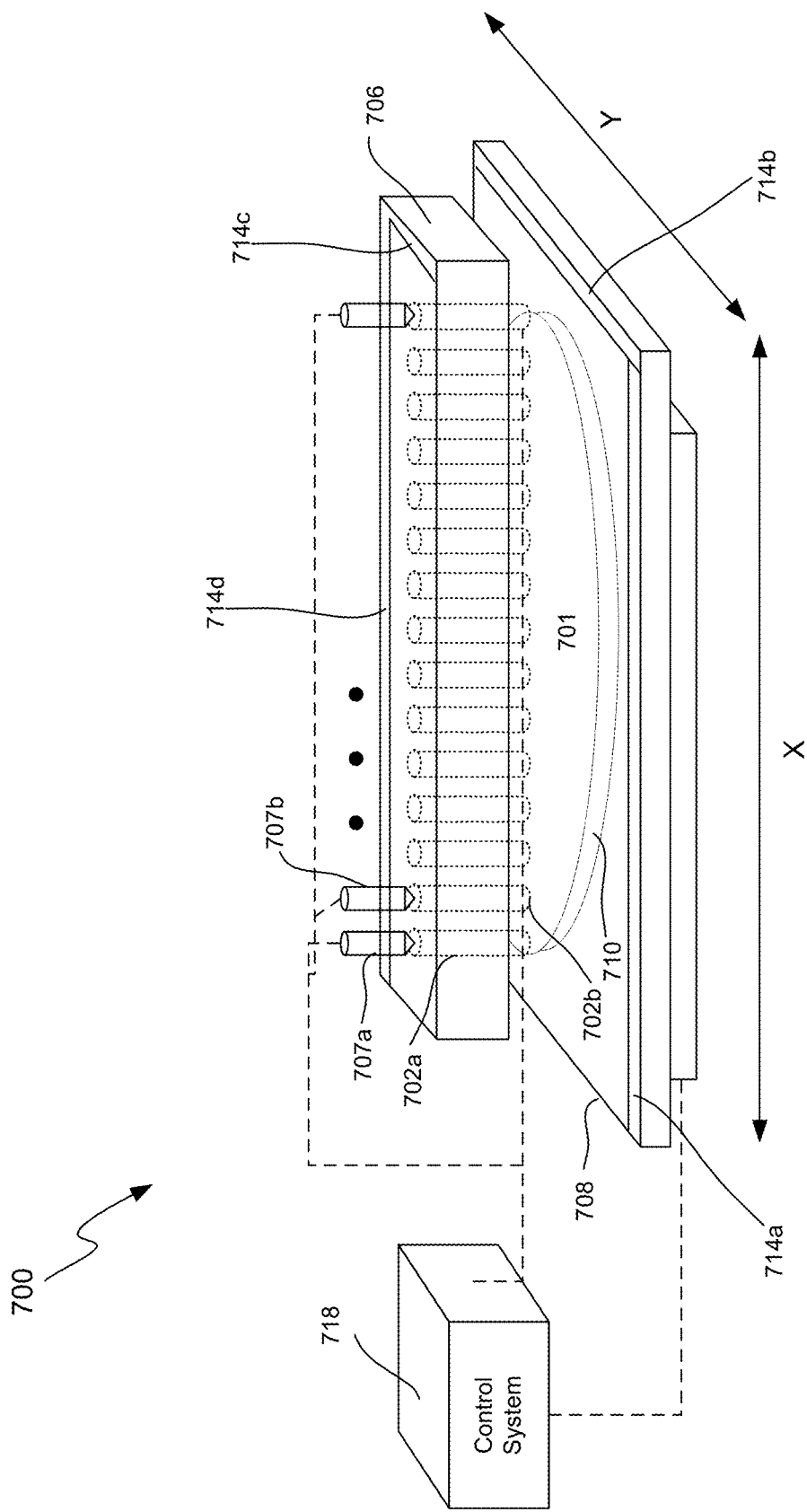
FIG. 7 is a diagrammatic representation of a distributed high-resolution system suitable for focusing charged-particles in multiple columns in accordance with a specific implementation of the present invention.

Any suitable high-resolution, distributed inspection tool may be implemented for separating potential defect and nuisance sites in a 1$^{st}$ stage as described herein. Referring generally to FIG. 7, a distributed high-resolution system 700 suitable for focusing charged-particles in multiple probes is described in accordance with a specific implementation of the present invention. In one example, the system 700 includes a plurality of probes (e.g., 702a and 702b) arranged in a linear array support 706. A plurality of charged particle sources (e.g., 707a and 707b) may be arranged to generate and direct a charged particle beams towards each of the probes with each directing its corresponding charged particle beam towards the sample (e.g., wafer 701). Alternatively, each source may be integrated with each probe. Each charged particle source may include any source known in the art. For example, the source 902 may include, but is not limited to, one or more electron guns.

Each probe or column may include any number of lens(es) and components for focusing its corresponding beam, emitted by its respective charged particle source, a deflector that scans its beam across a defect area of the wafer sample, and a detector that detects emissions from the wafer sample in response to the impinging charged particle beam and forms a high-resolution image. In one aspect, each column in the lens array is a miniature MEMS-based column.

In some embodiments, each column may further include a set of electron-optic elements. The set of electron-optics may include any electron-optic elements known in the art suitable for focusing and/or directing the electron beam onto a selected portion of the sample 701. In one embodiment, the set of electron-optics elements includes one or more electron-optic lenses. For example, the electron-optic lenses may include, but are not limited to, one or more condenser lenses for collecting electrons from the electron beam source. By way of another example, the electron-optic lenses may include, but are not limited to, one or more objective lenses for focusing the corresponding electron beam onto a selected region of the sample 701. In some embodiments, each electron beam may be directed to the sample 701 at a controlled angle. Because the provided wafer system coordinates does not necessarily coincide with SEM system of coordinates, controlling a fine scan angle may improve matching between the coordinate systems and significantly contribute to sampling performance/accuracy.

In some embodiments, the set of electron-optics elements for each column includes one or more electron beam scanning elements. For example, the one or more electron beam scanning elements may include, but are not limited to, one or more scanning coils or deflectors suitable for controlling a position of the beam relative to the surface of the sample 701. In this regard, the one or more scanning elements 916 may be utilized to scan the electron beam across the sample 701 in a selected scan direction or pattern. For example, the sample 701 may be scanned in tilted or perpendicular bidirectional scans relative to feature placement (e.g., at bidirectional directions and angled with respect to target lines) of certain structures. A controller system 718 may be communicatively coupled to one or more of the electron-optic elements, such as the one or more scanning elements. Accordingly, the controller system 718 may be configured to adjust one or more electron-optic parameters and/or control the scan direction via a control signal transmitted to each set of communicatively coupled electron-optic elements.

In some embodiments, each column may include (or be associated with) a detector assembly for each column that includes an electron collector (e.g., secondary electron collector). The detector assembly may further include an energy filter based, for example, on retarding field principle. In this regard, the energy filter may be configured to stop low energy secondary electrons while passing high energy secondary electrons (i.e., backscattered electrons). If the energy filter is not activated, all secondary electrons are detected according to collection efficiency of the detection system. By subtracting high energy electron image from overall electron image, low energy secondary electron image can be obtained. The detector assembly may further include a detector (e.g., scintillating element and PMT detector) for detecting electrons from the sample surface (e.g., secondary electrons).. In some embodiments, the detector of the detector assembly includes a light detector. For example, the anode of a PMT detector of the detector may include a phosphor anode, which is energized by the cascaded electrons of the PMT detector absorbed by the anode and may subsequently emit light. In turn, the light detector may collect light emitted by the phosphor anode in order to image the sample 906. The light detector may include any light detector known in the art, such as, but not limited to, a CCD detector or a CCD-TDI detector. The system 700 may include additional/alternative detector types such as, but not limited to, Everhart-Thornley type detectors.

While the foregoing description is focused on each detector assembly in the context of the collection of secondary electrons, this should not be interpreted as a limitation on the present invention. It is recognized herein that each detector assembly may include any device or combination of devices known in the art for imaging or characterizing a sample surface or bulk with a charged particle beam. For example, each detector assembly may include any particle detector known in the art configured to collect backscattered electrons, Auger electrons, transmitted electrons or photons (e.g., x-rays emitted by surface in response to incident electrons).

The wafer sample 701 is supported on a chuck 710, which is coupled with a stage 708. In typical arrangements, the stage has a rotatable chuck upon which the wafer is positioned and affixed. The stage 701, chuck 710, and/or array support 706 in certain embodiments can be configured with a movement mechanism to move in one or more directions, including X, Y, Z, tilt, and rotational directions. Each column may be movable together or independently. These movement mechanisms may take the form of both course and fine grade movement mechanisms that are driven by one or more screw drive and stepper motors, linear drives with feedback position, band actuator and stepper motors, magnetic fields, etc. The movement mechanisms may also implement roller bearings, air bearings, sliding plastic bearings, flexure suspension or magnetic field suspension, etc. In other embodiments, the column system can alternatively or additionally move in one more directions, including X, Y, Z, tilt, and rotational directions. An interferometer mirror may be positioned along each of the movement directions with the stage 708 and/or array support 706 as exemplified with respect to the embodiments of FIGS. 4A-E. In FIG. 7, mirrors 714a and 714b are positioned on each X and Y axis of the stage 708, and mirrors 714c and 714d are positioned on each X and Y axis of the array support 708. The mirrors form part of the interferometer system for accurately determining site locations. If either the stage or array does not move, its corresponding mirrors may be removed.

The controller system 718 may be configured for controlling any suitable components of the system 700, as well as receiving and processing high resolutions images acquired by the detectors of the columns. The control system 718 may be communicatively coupled to various components of the system 700. The control system may include one or more processors and electronic components for control, processing, and analysis.

The control system 718 may be configured to adjust one or more charged particle source parameters via a control signal to the each source. For example, the control system 718 may be configured to vary the beam current for an electron beam emitted by each source via a control signal transmitted to control circuitry of the electron beam source.

In some embodiments, the control system 718 is communicatively coupled to the sample stage 708 and/or column assembly. The control system 718 may be configured to adjust one or more stage parameters via a control signal transmitted to the sample stage 708. The control system 718 may be configured to vary the sample scanning speed and/or control the scan direction via a control signal transmitted to control circuitry of the sample stage 708 and/or column assembly. For example, the control system 718 may be configured to vary the speed and/or control the direction with which sample 701 and/or column assembly are linearly translated (e.g., x-direction or y-direction).

In some embodiments, the control system 718 is communicatively coupled to each detector or detector assembly. The control system 718 may be configured to adjust one or more image forming parameters via a control signal transmitted to each detector. For example, the control system 718 may be configured to adjust the extraction voltage or the extraction field strength for the secondary electrons.

Those skilled in the art will appreciate that "the control system 718 " may include one or more computing systems or controllers, such as one or more processors configured to execute one or more instruction sets embedded in program instructions stored by at least one non-transitory signal bearing medium. The computing system 924 may control various scanning The control system 718 may be configured to receive and/or acquire data or information (e.g., detected signals/ images, statistical results, reference or calibration data, training data, models, extracted features or transformation results, transformed datasets, curve fittings, qualitative and quantitative results, etc.) from other systems by a transmission medium that may include wireline and/or wireless portions. In this manner, the transmission medium may serve as a data link between the control system 718 and other systems (e.g., memory on-board inspector system, external memory, reference inspector source, or other external systems). For example, control system 718 may be configured to receive site locations from the optical inspector from a storage medium (e.g., internal or external memory) via a data link. For instance, results obtained using the inspector 700 system may be stored in a permanent or semi-permanent memory device (e.g., internal or external memory). In this regard, the results may be imported from on-board memory or from an external memory system. Moreover, the control system 718 may send data to other systems via a transmission medium. For instance, qualitative and/or quantitative results, such as metrology values, determined by control system 718 may be communicated and stored in an external memory. In this regard, candidate defect data results may be exported to another system.

Control system 718 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium. Program instructions may be stored in a computer readable medium (e.g., memory). Exemplary computer-readable media include read-only memory, a random access memory, a magnetic or optical disk, or a magnetic tape.

Computational algorithms are usually optimized for metrology applications with one or more approaches being used such as design and implementation of computational hardware, parallelization, distribution of computation, load-balancing, multi-service support, dynamic load optimization, etc. Different implementations of algorithms can be done in firmware, software, FPGA, programmable optics components, etc.

A separate high-resolution system may be used for defect review. This system will generally have a higher resolution than the $2^{nd}$ stage inspector. In an alternative embodiment, the $2^{nd}$ stage inspector may include one or more columns that are specifically configured to achieve a higher resolution than the other scanning columns. In an electron beam column example, the system, which is either a part of the $2^{nd}$ stage system or separate from the $2^{nd}$ stage system, is configured to apply a lower current to the reviewing column, as compared to current applied to the $2^{nd}$ stage columns' currents, so that the reviewing column achieves a relatively higher resolution than the $2^{nd}$ stage columns. In other embodiments, the higher-resolution probe system and the high-resolution distributed probe system may be different types of systems, such as AFM probe for the higher resolution system and an electron beam system for the distributed probes or any combination of probes described herein.

Certain embodiments of the present invention presented here generally address the field of semiconductor inspection and process control, and are not limited to the hardware, algorithm/software implementations and architectures, and use cases summarized above.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A method of detecting defects on a semiconductor sample, the method comprising:
   using an optical inspector to inspect a semiconductor sample with an aggressively predefined threshold selected to detect a plurality of candidate defect and nuisance sites at a plurality of corresponding locations across the sample, wherein the plurality of candidate defect and nuisance sites and their locations are provided to a high-resolution distributed probe inspector;
   using the high-resolution distributed probe inspector to inspect the plurality of candidate defect and nuisance sites on the sample to separate the candidate defect sites from the nuisance sites, wherein the high-resolution distributed probe inspector comprises an array of high-resolution probes, and wherein the high-resolution distributed probe inspector is configured to move the array of probes relative to the sample and the array of probes are configured to scan and obtain a high-resolution image of each site so as to separate the candidate defect sites from the nuisance sites;
   using a higher-resolution probe to obtain a higher-resolution image of each candidate site, wherein the higher-resolution probe has a higher resolution than a resolution of the high-resolution probes that are configured to obtain a high-resolution image of each site; and
   reviewing each candidate defect's higher-resolution image to separate real defects that adversely impact operation of any devices on the sample from the candidate defects.

2. The method of claim 1, wherein the high-resolution distributed probe inspector includes the higher-resolution probe.

3. The method of claim 1, wherein:
   the optical inspector is used and configured with a resolution that is between about 300 nm to 500 nm
   the miniature high-resolution probes each has a resolution that is below about 10 nm and the array of probes are configured to scan each site while the stage moves; and
   the higher resolution probe has a resolution that is about 1 nm or less.

4. The method of claim 1, wherein the sites detected by the optical inspector number in the millions and the candidate defect sites number in the thousands or less, and wherein using the high-resolution distributed probe inspector to inspect the candidate defect and nuisance sites on the sample to separate the candidate defect sites from the nuisance sites takes an hour or less.

5. The method of claim 1, wherein the miniature high-resolution probes: is arranged in a linear array that spans the semiconductor sample, number between 10 to 100 probes, and
   comprised of their own objectives and scanning electronics to scan the individual sites.

6. The method of claim 1, wherein the high-resolution distributed probe inspector comprises a stage upon which the semiconductor sample is loaded, and the stage is configured to scan swaths of the semiconductor sample under each of the miniature high-resolution probes, which remain stationary, so as to provide full semiconductor sample coverage.

7. The method of claim 1, wherein the high-resolution distributed probe inspector comprises a stage upon which the semiconductor sample is loaded, and the miniature high-resolution probes are movable and configured to scan over swaths of the semiconductor sample while the stage remains fixed.

8. The method of claim 1, wherein the high-resolution distributed probe inspector comprises a stage upon which the semiconductor sample is loaded, and the stage and the miniature high-resolution probes are both movable and configured to scan swaths of the semiconductor sample under each of the miniature high-resolution probes.

9. The method of claim 8, wherein the miniature high-resolution probes are configured to move radially while the stage is configured to rotate, and the swaths are circular.

10. The method of claim 8, wherein the miniature high-resolution probes are arranged in a plurality of spokes to be centered over the semiconductor sample and each spoke is configured to move radially while the stage is configured to rotate, and the swaths are circular.

11. The method of claim 1, wherein the high-resolution distributed probe inspector is a scanning electron microscope (SEM), and each probe of the miniature high-resolution probes comprises microelectromechanical system technology.

12. The method of claim 1, wherein the miniature high-resolution probes comprise multiple atomic force microscope (AFM) probes, or multiple near-field microwave probes, multiple proximal optical probes.

13. A hybrid inspector system for detecting defects on a semiconductor sample, comprising:
   an optical inspector configured to inspect a semiconductor sample with an aggressively predefined threshold selected to detect a plurality of candidate defect and nuisance sites at a plurality of corresponding locations across the sample, wherein the plurality of candidate defect and nuisance sites and their locations are provided to a high-resolution distributed probe inspector;
   the high-resolution distributed probe inspector configured to inspect the plurality of candidate defect and nuisance sites on the sample to separate the candidate defect sites from the nuisance sites, wherein the high-resolution distributed probe inspector comprises an array of miniature high-resolution probes, and wherein the high-resolution distributed probe inspector is configured to move the array of probes relative to the sample and the probes are configured to scan and obtain a high-resolution image of each site so as to separate the candidate defect sites from the nuisance sites; and a higher-resolution probe configured to:
   obtain a higher-resolution image of each candidate site, wherein the higher-resolution probe has a higher resolution than a resolution of the high-resolution probes that are configured to obtain a high-resolution image of each site, and review each candidate defect's higher-resolution image to separate real defects that adversely impact operation of any devices on the sample from the candidate defects.

14. The system of claim 13, wherein the high-resolution distributed probe inspector includes the higher-resolution probe.

15. The system of claim 13, wherein:

the optical inspector configured with a resolution that is between about 200 nm to 500 nm the miniature high-resolution probes each has a resolution that is below about 10 nm and the array of probes are configured to scan each site while the stage moves; and the higher resolution probe has a resolution between about 1nm or less.

16. The system of claim 13, wherein the sites detected by the optical inspector number in the millions and the candidate defect sites number in the thousands or less, and wherein the high-resolution distributed probe inspector is configured to inspect the candidate defect and nuisance sites on the sample to separate the candidate defect sites from the nuisance sites in an hour or less.

17. The system of claim 13, wherein the miniature high-resolution probes: is arranged in a linear array that spans the semiconductor sample, number between 10 to 100 probes, and comprised of their own objectives and scanning electronics to scan the individual sites.

18. The system of claim 13, wherein the high-resolution distributed probe inspector comprises a stage upon which the semiconductor sample is loaded, and the stage is configured to scan swaths of the semiconductor sample under each of the miniature high-resolution probes, which remain stationary, to provide full semiconductor sample coverage.

19. The system of claim 13, wherein the high-resolution distributed probe inspector comprises a stage upon which the semiconductor sample is loaded, and the miniature high-resolution probes are movable and configured to scan over swaths of the semiconductor sample while the stage remains fixed.

20. The system of claim 13, wherein the high-resolution distributed probe inspector comprises a stage upon which the semiconductor sample is loaded, and the stage and the miniature high-resolution probes are both movable and configured to scan swaths of the semiconductor sample under each of the miniature high-resolution probes.

21. The system of claim 20, wherein the miniature high-resolution probes is configured to move radially while the stage is configured to rotate, and the swaths are circular.

22. The system of claim 20, wherein the miniature high-resolution probes are arranged in a plurality of spokes to be centered over the semiconductor sample and each spoke is configured to move radially while the stage is configured to rotate, and the swaths are circular.

23. The system of claim 13, wherein the high-resolution distributed probe inspector is a scanning electron microscope (SEM), and each probe of the miniature high-resolution probes comprises microelectromechanical system technology.

24. The system of claim 13, wherein the miniature high-resolution probes comprise multiple atomic force microscope (AFM) probes, multiple near-field probes, or multiple proximal optical probes.

* * * * *

UNITED STATES PATENT AND TRADEMARK OFFICE
CERTIFICATE OF CORRECTION

PATENT NO. : 10,545,099 B1  
APPLICATION NO. : 16/272905  
DATED : January 28, 2020  
INVENTOR(S) : Chen et al.

Page 1 of 1

It is certified that error appears in the above-identified patent and that said Letters Patent is hereby corrected as shown below:

In the Claims

In Claim 12, Column 20, Line 43, change: "(AMF) probes, or multiple" to -- (AMF) probes, multiple --

In Claim 12, Column 20, Line 44, change: "probes, mulitple" to -- probes, or multiple --

Signed and Sealed this  
Twenty-fourth Day of March, 2020

Andrei Iancu  
*Director of the United States Patent and Trademark Office*